United States Patent [19]

Achiwa et al.

[11] Patent Number: 4,985,567

[45] Date of Patent: Jan. 15, 1991

[54] CHIRAL PHOSPHINOPYRROLIDINE COMPOUNDS AND THEIR USE FOR ASYMMETRIC SYNTHESIS OF OPTICALLY ACTIVE COMPOUNDS

[75] Inventors: Kazuo Achiwa, Shizuoka; Hideo Takeda, Takaoka, both of Japan

[73] Assignees: Kazuo Achiwa, Shizuoka; Fuji Yakuhin Kogyo Kabushiki Kaisha, Toyama, both of Japan

[21] Appl. No.: 319,186

[22] Filed: Mar. 6, 1989

[30] Foreign Application Priority Data

Mar. 7, 1988 [JP] Japan .................................. 63-53384
Apr. 2, 1988 [JP] Japan .................................. 63-81890
Oct. 4, 1988 [JP] Japan .................................. 63-250290

[51] Int. Cl.$^5$ .................. C07F 69/6518; C07B 53/00; B01J 31/02
[52] U.S. Cl. ............................ 548/412; 564/415; 568/881; 585/277
[58] Field of Search .................................. 548/412

[56] References Cited

U.S. PATENT DOCUMENTS

| | | | |
|---|---|---|---|
| 4,168,381 | 9/1979 | Fischer, Jr. .................. | 548/320 |
| 4,343,741 | 8/1982 | Townsend .................. | 548/412 |
| 4,409,397 | 10/1983 | Paxton .................. | 560/57 |
| 4,424,312 | 1/1984 | Stille .................. | 548/412 |
| 4,539,411 | 9/1985 | Broger .................. | 548/412 |
| 4,652,657 | 3/1987 | Broger .................. | 548/402 |
| 4,879,389 | 11/1989 | Achiwa .................. | 548/412 |

*Primary Examiner*—Mark L. Berch
*Attorney, Agent, or Firm*—Birch, Stewart, Kolasch and Birch

[57] ABSTRACT

New chiral phosphinopyrrolidine compounds of the general formula:

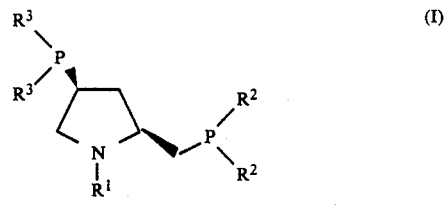

(I)

or

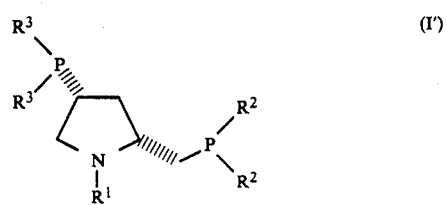

(I')

wherein $R^1$ is hydrogen or $-COA^1$, $-COOA^2$, $-CONHA^3$, $-SO_2A^4$ or $-PO(A^5)_2$, $A^1$, $A^2$, $A^3$, $A^4$ and $A^5$ each represents independently alkyl or aryl, $R^2$ is phenyl, di(lower-alkyl)aminophenyl, lower-alkoxyphenyl or 3,5-dimethyl-4-methoxyphenyl, and $R^3$ is phenyl, lower-alkylphenyl, di(lower-alkyl)aminophenyl, lower-alkoxyphenyl or 3,5-dimethyl-4-methoxyphenyl, with the proviso that $R^2$ and $R^3$ may not simultaneously by phenyl, p-di(lower-alkyl)-aminophenyl or p-lower-alkoxyphenyl, as well as the use of these compounds as ligand for a metal complex catalyst for asymmetric synthesis of optically active compounds. The new chiral phosphinopyrrolidine compounds are useful ligands which attain both of high optical yield and high reaction efficiency in catalytic asymmetric reduction.

4 Claims, No Drawings

CHIRAL PHOSPHINOPYRROLIDINE COMPOUNDS AND THEIR USE FOR ASYMMETRIC SYNTHESIS OF OPTICALLY ACTIVE COMPOUNDS

BACKGROUND OF THE INVENTION

1. Field of the Invention

The present invention relates to new chiral phosphinopyrrolidine compounds and to the use of these compounds as a ligand for a metal complex compound utilizable as a catalyst for asymmetric synthesis. More particularly, the present invention relates to new chiral 2,4-diphosphinopyrrolidine compounds and to the use of these compounds as a ligand for a metal complex compound utilizable as a catalyst for a process for the asymmetric synthesis of optically active compounds by catalytic asymmetric hydrogenation of reducible compounds.

2. Description of the Prior Art

From the past, a number of researches have been made in the field of synthetic chemistry on asymmetric reducing reaction capable of synthesizing optically active compounds directly from optically inactive reducible compounds. In one of the researches, various bisphosphine ligands have been synthesized and an asymmetric reducing reaction of a reducible compound has been tested using various combinations of such ligands with a transition metal compound as catalyst. In such asymmetric reducing reaction, an optical yield (asymmetric yield) of the product and a reaction efficiency in the reaction are taken up as important factors to evaluate whether the ligand is advantageously utilizable for such reaction or not. The optical yield is the simplest way for knowing whether the ligand is effective for preparing optically active products or not. With respect to the reaction rate, a larger amount of the ligand becomes necessary in case the reaction rate is low. As a means for knowing such relation between the amount of the ligand and the reaction rate, the reaction efficiency is defined by a ratio of the substrate to the ligand in terms of molar ratio. In such asymmetric reducing reactions, however, there is not as yet found such a ligand as satisfies both of the optical yield and the reaction efficiency at the same time (B. Bosnich, "Asymmetric Catalysis" published by Martinus Nijhoff Publishers, Boston, 1986, pp. 19–31).

Under such circumstances, there is a great demand in the field of asymmetric reducing reactions for developing a new ligand which satisfies not only the optical yield but also the reaction efficiency when used as a catalyst with a metal complex for asymmetric reducing reaction of reducible compounds.

BRIEF SUMMARY OF THE INVENTION

Accordingly, it is an object of the present invention to provide new chiral 2,4-diphosphinopyrrolidine compounds useful as a ligand for catalytic asymmetric hydrogenation.

It is another object of the present invention to provide the use of the 2,4-diphosphinopyrrolidine compounds as ligands in catalysts for asymmetric hydrogenation.

It is still another object of the present invention to provide a process for the asymmetric synthesis of optically active compounds by asymmetric hydrogenation of keto or unsaturated compounds.

Other and further objects, features and advantages of the present invention will become apparent more fully from the following description.

As a result of extensive researches made for developing new compounds useful as ligands which can afford a satisfactory optical yield and a reaction efficiency in asymmetric synthesis of optically active compounds, it has now been found that new 2,4-diphosphinopyrrolidine compounds are useful as ligands which show high levels of optical yield and reaction efficiency when used together with a transition metal compounds as catalyst for asymmetric hydrogenation of reducible compounds.

In accordance with one embodiment of the present invention, there is provided new chiral phosphinopyrrolidine compounds of the general formula:

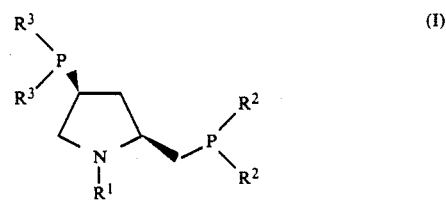

(I)

or

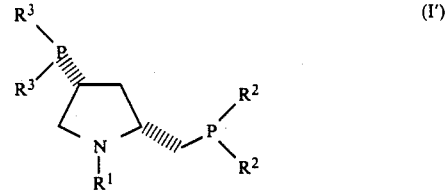

(I')

wherein $R^1$ is hydrogen or $-COA^1$, $-COOA^2$, $-CONHA^3$, $-SO_2A^4$ or $-PO(A^5)_2$, $A^1$, $A^2$, $A^3$, $A^4$ and $A^5$ each represents independently alkyl or aryl, $R^2$ is phenyl, di(lower-alkyl)aminophenyl, lower-alkoxyphenyl or 3,5-dimethyl-4-methoxyphenyl, and $R^3$ is phenyl, lower-alkylphenyl, di(lower-alkyl)-aminophenyl, lower-alkoxyphenyl or 3,5-dimethyl-4-methoxyphenyl, with the proviso that $R^2$ and $R^3$ may not simultaneously be phenyl, p-di(lower-alkyl)aminophenyl or p-lower-alkoxyphenyl.

In accordance with another embodiment of the present invention, there is provided the use of these new chiral phosphinopyrrolidine compounds as a ligand for a metal complex compound utilizable as a catalyst for a process for the asymmetric synthesis of compounds having asymmetric carbon atoms by catalytic hydrogenation of a reducible compound having a carbon-to-carbon double bond, carbon-to-nitrogen double double bond and/or carbon-to-oxygen double bond in the molecular structure thereof.

The new compounds and their use as ligands for asymmetric synthesis have various features as compared with similar ligands and their use for asymmetric synthesis in the prior arts. The new phosphinopyrrolidine compounds of this invention were developed on the basis of a quite new technical concept found during the present inventor's researches and constitute excellent ligands for asymmetric hydrogenation reactions. Thus, the new phosphinopyrrolidine compounds of this invention attain satisfactorily high levels of optical yield and reaction efficiency at the same time in asymmetric hydrogenation.

DETAILED DESCRIPTION OF THE INVENTION

As a result of the present inventor's extensive researches made on the reaction mechanism of ligands of phosphine series, it has been manifested that a moiety capable of increasing an optical yield of the product and a moiety capable of enhancing the reaction efficiency exist in the molecular structure of the ligands. More particularly, it has been made clear by a result of the present inventor's study that the phosphinopyrrolidine compound of the general formula (I) or (I') possessing especially remarkable properties as a ligand contains a phosphine grouping of the formula: $P(R^2)_2$ which gives influence on the increase of the optical yield and a phosphino grouping of the formula: $P(R^3)_2$ which gives influence on the enhancement of the reaction efficiency.

The present inventor already synthesized BPPM [(2S,4S)-N-tert.-butoxycarbonyl-4-diphenylphosphino-2-diphenylphosphinomethylpyrrolidine] as a chiral bisphosphine and used it as a combination with rhodium 1,5-cyclooctadiene chloride complex for asymmetric hydrogenation of ketopantolactone whereby R-(−)-pantolactone was obtained in an optical yield of 80.5% (Japanese Examined Patent Publication No. SHO 62-45238). The optical yield of the product in this case is relatively good but the reaction efficiency, being 100 (= substrate/Rh molar ratio), was found to be unsatisfactory in industrial point of view.

John Melvin Townsend et al. synthesized compounds which correspond to BPPM except in that the four phenyl groups are replaced by p-tolyl, p-di(lower-alkyl)amino phenyl or p-lower-alkoxyphenyl groups, and used them for improvement of reaction efficiency in the asymmetric hydrogenation but only at the sacrifice of the optical yield (Japanese Unexamined Patent Publication No. SHO-57-181093).

In accordance with his consideration on the coordination structure of the bisphosphine-rhodium complex, the present inventor synthesized a variety of phosphinopyrrolidine compounds, surmising that the phosphine group (in position 2) located in the cis-position to a functional group subjected to asymmetric reaction will give influence on the optical yield of the product while the phosphine group (in position 4) located in the trans position to the functional group will give influence on the reaction efficiency (reaction rate).

As a result of this, it was found that when the asymmetric reduction of ketopantolactone is carried out with BCPM [(2S,4S)-N-tert.-butoxycarbonyl-4-dicyclohexylphosphino-2-diphenylphosphinomethylpyrrolidine] as a combination with rhodium 1,5-cyclooctadiene chloride complex, R-(−)-pantolactone is obtained in an optical yield of 91–95% at a reaction efficiency of substrate/Rh=$10^5$ (molar ratio) and thus revealed that the reduction reaction is excellent in both optical yield and reaction efficiency to be carried out in an industrial scale (Japanese Unexamined Patent Publication No. SHO 63-5094).

BCPM, however, is expensive in that it is synthesized in fourteen steps from L-hydroxyproline.

The present inventor thus made extensive researches for ligands which can be synthesized in fewer steps at lower cost but, as in the case of BCPM, in excellent manner with respect to both optical yield and reaction efficiency.

As a result of this, the new phosphinopyrrolidine compounds of the general formula (I) or (I') mentioned above have been found to fulfill these objectives.

For example, in the case of the preparation of R-(−)-pantolactone as in Synthesis No. 7, an optical yield of 89% and a reaction efficiency of substrate/Rh=1000 (molar ratio), it thus being revealed that the reduction reaction is excellent in both optical yield and reaction efficiency to be carried out in an industrial scale.

In the phosphinopyrrolidine of the general formula (I) or (I') mentioned above, the radicals $A^1$, $A^2$, $A^3$, $A^4$ and $A^5$ each represents alkyl or aryl. Illustrative of the alkyl group are $C_1$–$C_6$ alkyl groups such as methyl, ethyl, propyl, isopropyl, n-butyl, sec.-butyl and tert.-butyl. Illustrative of the aryl group are phenyl and pyridyl. These alkyl and aryl groups may have one or more halogen atoms such as fluorine or chlorine, hydroxyl groups, alkyl groups and alkoxy groups as substituents.

The radical $R^2$ represents phenyl, di(lower-alkyl)aminophenyl, lower-alkoxyphenyl or 3,5-dimethyl-4-methoxyphenyl. Examples of the di(lower-alkyl)aminophenyl group include 2-dimethylaminophenyl, 3-dimethylaminophenyl and 4-dimethylaminophenyl, and those of the lower-alkoxyphenyl group include 2-methoxyphenyl, 3-methoxyphenyl, 4-methoxyphenyl and 2,4-dimethoxyphenyl.

The radical $R^3$ represents phenyl, lower-alkylphenyl, di(lower-alkyl)aminophenyl, lower-alkoxyphenyl or 3,5-dimethyl-4-methoxyphenyl. Examples of the di(lower-alkyl)aminophenyl and lower-alkoxyphenyl groups include those as exemplified above, and those of the lower-alkylphenyl group include 2-tolyl, 4-tolyl and 2,4-dimethylphenyl.

A process for the asymmetric synthesis of optically active compounds by catalytic reduction of the reducible compounds with the aid of the new phosphinopyrrolidine compounds of this invention as ligands together with the reaction metal catalyst will now be explained hereinafter, taking up the asymmetric synthesis of pantolactone from ketopantolactone as an example.

A solvent generally employed for catalytic reduction can also be used for the asymmetric synthesis. For example, water, a water-miscible alcohol such as methanol, ethanol or isopropanol, acetic acid or propionic acid, an ester such as ethyl acetate, an ether such as tetrahydrofuran or dioxane, or an aromatic hydrocarbon such as benzene or toluene can be used advantageously. In 50 ml of such solvent are dissolved 100 m-mol of ketopantolactone and 0.2–0.001 m-mol of a phosphinopyrrolidine compound of this invention as a ligand. A rhodium metal complex compound such as rhodium 1,5-hexadiene chloride complex or rhodium 1,5-cyclooctadiene chloride complex in an amount of 0.05–0.0005 m-mol is added to the solution and the mixture is subjected to hydrogenation reaction at atmospheric or super-atmospheric pressure at a reaction temperature, preferably, of 0°–100° C. After completion of the reaction, the solvent used is distilled off and the residual substance is worked up properly whereupon (R)-(−)-pantolactone can be obtained as the product in a high yield.

The process will now also be explained taking up the asymmetric synthesis of (R)-N-acetylphenylalanine from α-acetamidocinnamic acid as another example.

In a solvent generally employed for catalytic reduction such as water, methanol, ethanol or isopropanol are dissolved a rhodium metal complex compound such as rhodium dinorbornadiene perchlorate and a phosphinopyrrolidine compound (I) as a ligand. A substrate is added to the solution and the mixture is hydrogenation at atmospheric or super-atmospheric pressure at a reaction temperature, preferably, of 0°–100° C., with the substrate/rhodium molar ratio being in the range of 200–1,000,000. The ligand/rhodium molar ratio is preferably 1–3. After completion of the reaction, the solvent used is distilled off and the residual substance is worked up properly whereupon (R)-N-acetylphenylalanine can be obtained as the product in a high yield.

The phosphinopyrrolidine compounds of the general formula (I) or (I') according to the invention may be prepared according to a series of the steps shown in Scheme 1, 2 or 3 wherein "Boc" stands for —COOC(CH₃)₂ and "Ts" for

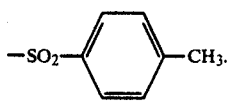

Scheme 1

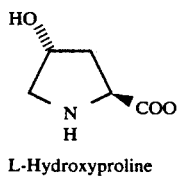

L-Hydroxyproline 4 steps ⟹

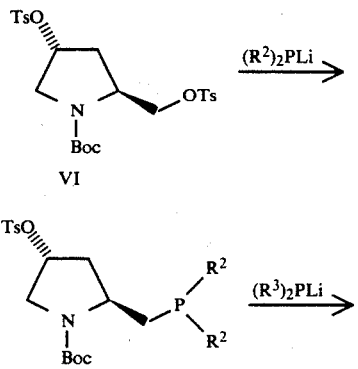

VI (R²)₂PLi →

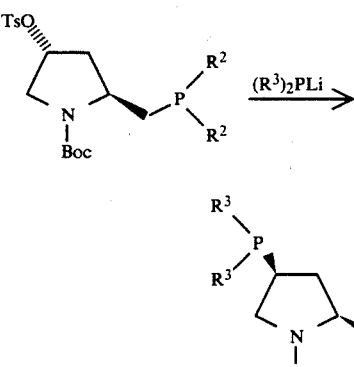

(R³)₂PLi →

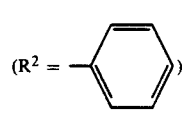

VII (R² = 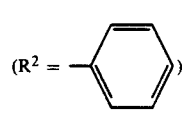)

(R² = 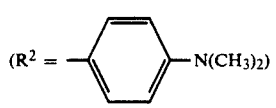)

-continued
Scheme 1

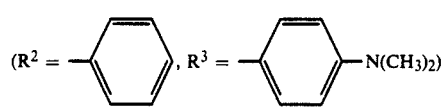

Ia

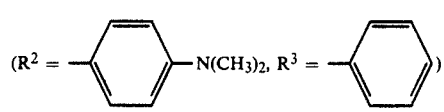

Ic

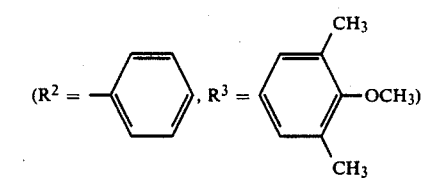

Ih

Scheme 2

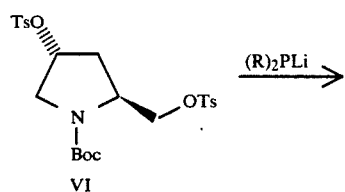

VI (R)₂PLi →

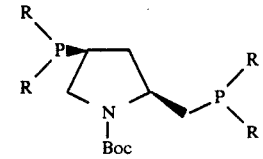

Id (R = 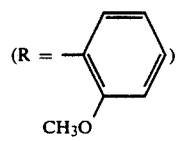)

Ie (R = 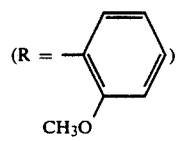)

If (R = 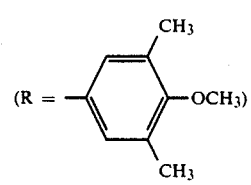)

Ii (R = 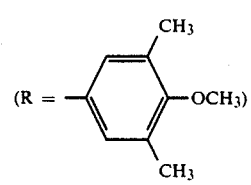)

Scheme 3

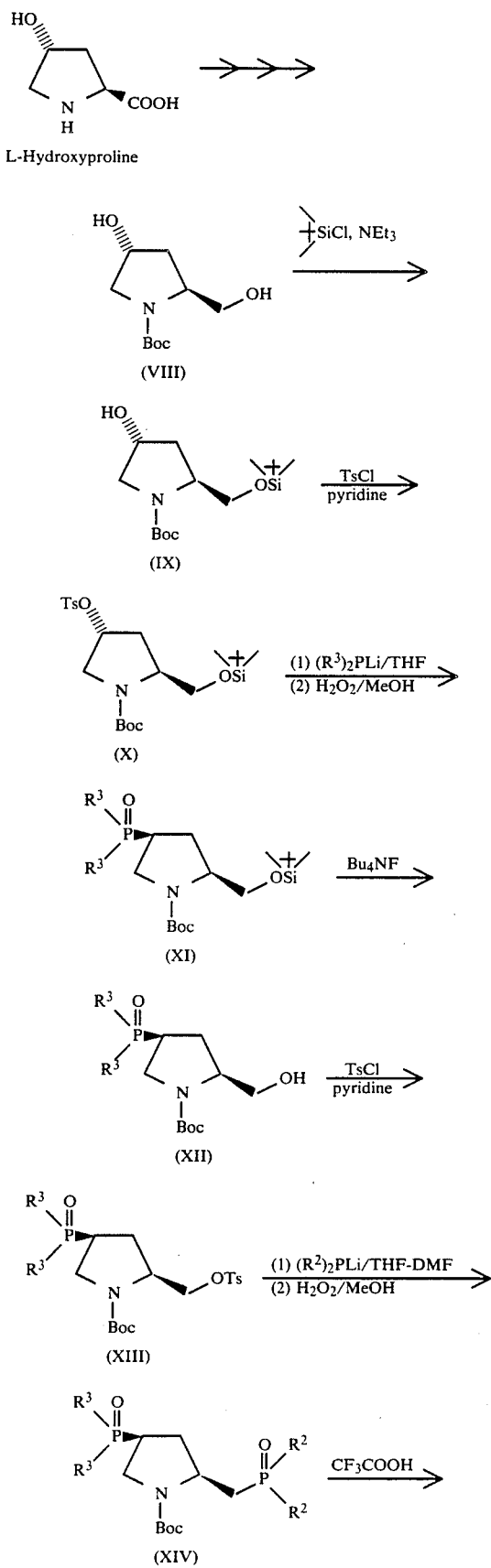

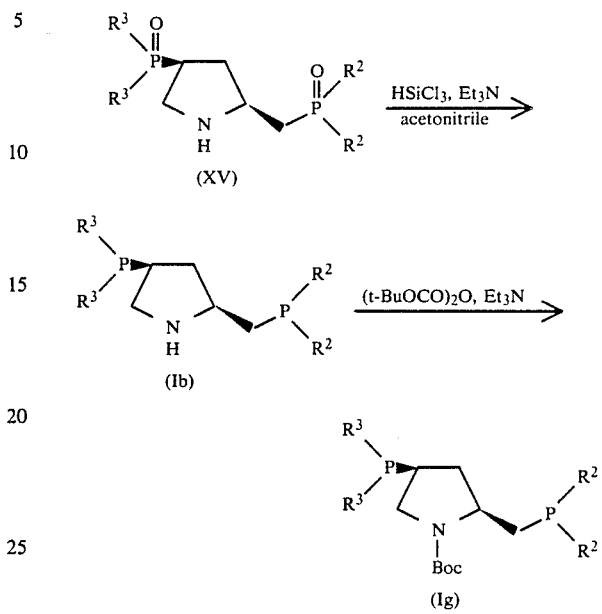

In Scheme 1, L-hydroxyproline is converted in four steps based on the manner described in the literatures into the ditosyl derivative (VI), which is then reacted with a diphenylphosphinolithium compound to form compound (VII) or (VIIc). After isolation and purification, compound (VII), for example, is reacted with bis(4-dimethylaminophenyl)-phosphinolithium to form compound (Ia). Compounds (Ic) and (Ih) may be obtained in the same manner. These compounds are treated with trifluoroacetic acid, and then brought into reaction with a halide or anhydride of a carboxylic, sulfonic or phosphonic acid or an isocyanate to give the corresponding compounds of the general formula (I). The corresponding compounds of the general formula (I') may be prepared in the same manner but using D-hydroxyproline instead of the L-hydroxyproline used in the steps mentioned above.

In Scheme 2, 2S,4S disubstituted phosphinopyrrolidine compounds are obtained by reacting the ditosyl derivatives (VI) with phosphinolithium compounds of the general formula: $(R)_2PLi$.

In Scheme 3, L-hydroproline is converted in five steps into compound (X) (referred to Jap. Pat. Publn. No. 62-45238), which is then reacted, for example, with bis(4-methoxyphenyl)-phosphinolithium as a compound of the formula $(R^3)_2PLi$. The resultant product is then oxidized to form oxide (XI). The alcohol protecting group in the 2-position of this oxide is removed and the product is tosylated to give compound (XIII). This compound is reacted, for example, with bis(2-methoxyphenyl)phosphinolithium as a compound of the formula $(R^2)_2PLi$ and the product is then oxidized to form compound (XIV). The Boc group on this compound is removed and the product is then reduced to form compound (Ib). Starting from compound (Ib), various compounds of the general formula (I) can easily be prepared by introducing thereinto an acyl, carbamoyl or phosphinyl group. Thus, for example, compound (Ig) can be obtained by introducing a Boc group into the N-position.

The present invention will now be illustrated in more detail by way of examples, which by no means limit the scope of the invention. These examples include those for the preparation of some of the new phosphinopyrrolidine compounds of this invention shown under the title "Examples" and those for the asymmetric synthesis with such compounds shown under the title "Synthesis". The preparation of the phosphine compounds to be used in "Examples" are exemplified as follows:

Preparation (1)

Under argon atmosphere, magnesium (4.25 g) was placed in tetrahydrofuran (hereinafter referred to as THF) (5 ml) and a solution of 4-bromo-N,N-dimethylaniline (25.0 g) in THF (150 ml) was added dropwise. The mixture was boiled under reflux for 30 minutes and, after ice-cooling, a solution of dichlorophenylphosphine (10.74 g) in THF (50 ml) was added dropwise. The mixture was stirred overnight at room temperature. After addition of a saturated aqueous solution of ammonium chloride, the reaction mixture was concentrated under reduced pressure and extracted with benzene. The benzene layer was washed with a saturated aqueous solution of sodium chloride, concentrated until dryness under reduced pressure and subjected to recrystallization from ethanol under argon atmosphere whereby 31 g of bis(4-dimethylaminophenyl)phenylphosphine, m.p. 85° C., was obtained.

To this product were added diisopropylamine (2.85 g) and THF (40 ml), and after the atmosphere was replaced by argon, lithium (389 mg) was added. The mixture was stirred at room temperature for 6 hours and, after addition of an ice-cooled, degassed, saturated aqueous solution of sodium chloride, extracted with benzene. The benzene layer was dried over magnesium sulfate, concentrated under reduced pressure and distilled under reduced pressure whereby 1.0 g of the desired product bis(4-dimethylaminophenyl)phosphine was obtained as b.p. 180°–190° C./3 torr fraction. m.p. 80°–90° C. (sealed tube).

Preparation (2)

Under argon atmosphere, magnesium (3.57 g) was placed in THF (5 ml) and a solution of o-bromoanisole (25.0 g) in THF (80 ml) was added dropwise. The mixture was stirred for 2 hours and a solution of phosphorus trichloride (3.04 g) in THF (70 ml) was added dropwise under ice-cooling. The mixture was stirred overnight at room temperature. Under ice-cooling, 5% hydrochloric acid (25 ml) was added dropwise. The crystals formed were filtered off and recrystallized from ethanol whereby 12.39 g of tris(2-methoxyphenyl)phosphine, m.p. 203°–204° C., was obtained.

In a separate reaction vessel and under argon atmosphere, potassium (945 mg) and sodium (228 mg) were added to degassed dioxane (10 ml) and the mixture was heated. After ice-cooling tris(2-methoxyphenyl)phosphine obtained above (4.00 g) and dioxane (40 ml) were added and the mixture was stirred for 3 hours at room temperature. After ice-cooling, tert.-butanol (10 ml) and methanol were added thereto. The mixture was concentrated under reduced pressure and, after addition of benzene, washed with a degassed saturated aqueous solution of sodium chloride. The benzene layer was dried over magnesium sulfate, concentrated under reduced pressure until dryness whereby 2.40 g of bis(2-methoxyphenyl)phosphine as a white solid.

Preparation (3)

In the same manner as described in Preparation (2) but using m-bromoanisole (25.0 g) instead of the o-bromoanisole used therein, the reaction and after-treatment were carried out whereby 11.76 g of bis(3-methoxyphenyl)phosphine was obtained as a white solid having a melting point of 113°–115° C.

Preparation (4)

Under argon atmosphere, magnesium (2.67 g) was placed in THF (5 ml) and a solution of 2,4-dimethoxyphenylbromide (21.7 g) in THF (50 ml) was added dropwise. The mixture was stirred for 1 hour and then a solution of diethyl phosphite (4.56 g) in THF (20 ml) was added dropwise under ice-cooling. The mixture was stirred overnight at room temperature, and then 5% hydrochloric acid (25 ml) was added dropwise under ice-cooling. The reaction mixture was extracted with benzene. The benzene layer was washed with a degassed saturated aqueous solution of sodium chloride, dried over magnesium sulfate and concentrated under reduced pressure until dryness. The residue was subjected to recrystallization from benzene whereby 9.06 g of bis(2,4-dimethoxyphenyl)phosphine oxide was obtained. 3.22 g of the product was dissolved in degassed toluene (36 ml) under argon atmosphere. The solution was ice-cooled and trichlorosilane (5.0 ml) was added thereto. The mixture was boiled under reflux and stirred for 5 hours and, after ice-cooling, 2N caustic soda (16 ml) was added thereto. The toluene layer was separated and the aqueous layer was extracted with toluene. The toluene layers were combined, dried over magnesium sulfate, concentrated under reduced pressure and distilled under reduced pressure whereby 1.53 g of bis(2,4-dimethoxyphenyl)phosphine was obtained as a fraction boiling at 240°–250° C./3 Torr (bulb-to-bulb).

Preparation (5)

Caustic soda (12.6 g) was dissolved in water (250 ml) and the solution was cooled to 15° C. Methylene chloride (250 ml), 2,6-dimethyl-4-bromophenol (40.21 g), tetrabutylammonium bromide (3.22 g) and dimethyl sulfate (64.35 g) were added thereto. The mixture was stirred at room temperature for 5.5 hours and, after addition of caustic soda (8.0 g), for a further period of 1 hour. The reaction mixture was phase-separated and the aqueous layer was extracted with methylene chloride. The methylene chloride layers were combined and concentrated. The concentrate was dissolved in isopropyl ether and the solution was washed successively with 2N aqueous ammonia, a 2N aqueous solution of caustic soda and a saturated aqueous solution of sodium chloride. After phase separation, the aqueous layer was extracted with isopropyl ether. The organic layers were combined, dried over anhydrous magnesium sulfate, concentrated under reduced pressure and distilled under reduced pressure whereby 2,6-dimethyl-4-bromoanisole (40.15 g), b.p. 129°–130° C./42 Torr.

In a separate reaction vessel and under argon atmosphere, magnesium (4.68 g) was placed in THF (5 ml) and a solution of 2,6-dimethyl-4-bromoanisole (37.64 g) in THF (110 ml) was added dropwise. The mixture was stirred for 3 hours and a solution of diethyl phosphite (8.06 g) in THF (20 ml) was added dropwise under ice-cooling. The mixture was stirred overnight at room temperature and then boiled under reflux for 4 hours. Under ice-cooling, 5% hydrochloric acid (40 ml) was added dropwise and the mixture was extracted with benzene. The benzene layer was washed with a saturated aqueous solution of sodium chloride, dried over magnesium sulfate and concentrated under reduced pressure. The residue was purified by column chromatography on silica gel whereby 13.68 g of bis(3,5-dimethyl-4-methoxyphenyl)phosphine oxide was obtained. 3.40 g of this product was dissolved in degassed toluene (40 ml) under argon atmosphere. The solution was ice-cooled and then trichlorosilane (5.0 ml) was added thereto. The mixture was boiled under reflux and stirred for 5 hours. The reaction mixture was ice-cooled and then 2N caustic soda (100 ml) was added thereto. The toluene layer was separated and the aqueous layer was extracted with toluene. The toluene layers were combined, washed with a degassed saturated aqueous solution of sodium chloride, dried over magnesium sulfate, concentrated under reduced pressure and distilled under reduced pressure whereby 1.70 g of bis(3,5-dimethyl-4-methoxyphenyl)phosphine was obtained as a fraction boiling at 200°–210° C./2 Torr (bulb-to-bulb).

EXAMPLE 1

Under argon atmosphere, diphenylphosphine (2.13 g) was dissolved in THF (40 ml) and the solution was cooled to −40° C. 1.6M-n-butyllithium-hexane solution (7.5 ml) was added thereto and the mixture was stirred for 15 minutes to give a phosphine anion solution. (2S,4R)-N-tert.-butoxycarbonyl-4-tosyloxy-2-tosyloxymethylpyrrolidine (VI) (4.0 g) was dissolved in THF (60 ml) and DMF (10 ml) and the solution was cooled to −40° C. To this cooled solution was added dropwise the phosphine anion solution prepared above. The mixture was stirred overnight at −40° C., and subjected to filtration after celite (filter aid) was added thereto. The filtrate was concentrated and, after addition of a cold saturated aqueous solution of sodium bicarbonate, extracted with benzene. The benzene layer was dried over anhydrous magnesium sulfate and then concentrated. The residue was purified by column chromatography on silica gel (toluene/ethyl acetate) whereby 3.0 g of (2S,4R)-N-tert.-butoxycarbonyl-2-diphenylphosphinomethyl-4-tosyloxypyrrolidine (VII) was obtained.

Under argon atmosphere, bis(4-dimethylaminophenyl)phosphine (1.2 g) was dissolved in THF (10 ml) and the solution was cooled to −30° C. 1.6M-n-butyllithium-hexane solution (2.4 ml) was added thereto and the mixture was stirred for 30 minutes. 1.0 g of compound (VII) dissolved in THF (20 ml) was added dropwise at −30° C. The mixture was stirred overnight and then subjected to filtration after celite (filter aid) was added thereto. The filtrate was concentrated and, after addition of a cooled saturated aqueous solution of sodium bicarbonate, extracted with benzene. The benzene layer was dried over anhydrous magnesium sulfate and concentrated. The residue was purified by column chromatography on alumina (toluene-toluene/ethyl acetate) whereby 811 mg of (2S,4S)-N-tert.-butoxycarbonyl-4-bis(4-dimethylaminophenyl)phosphino-2-diphenylphosphinomethylpyrrolidine (see formula Ia) as an amorphous solid. $[\alpha]_D^{23} = -40.66°$ (c=0.7, benzene).

EXAMPLE 2

Under argon atmosphere, bis(4-dimethylaminophenyl)phosphine (1.0 g) was dissolved in THF (10 ml) and the solution was cooled to −40° C. 1.6M-n-butyllithium-hexane solution (2.5 ml) was added thereto and the mixture was stirred for 15 minutes to give a phosphine anion solution.

In a separate reaction vessel, (2S,4R)-N-tert.-butoxycarbonyl-4-tosyloxy-2-tosyloxymethylpyrrolidine (VI) (4.0 g) was dissolved in THF (20 ml) and the solution was cooled to −40° C. To this cooled solution was added dropwise the phosphine anion solution prepared above. The mixture was stirred overnight at −40° C. and subjected to filtration after celite (filter aid) was added thereto. The filtrate was concentrated and, after addition of a cold saturated aqueous solution of sodium bicarbonate, extracted with benzene. The benzene layer was dried over anhydrous magnesium sulfate and then concentrated. The residue was purified by column chromatography on alumina (toluene-toluene/ethyl acetate) whereby 1.12 g of (2S,4R)-N-tert.-butoxycarbonyl-2-bis(4-dimethylaminophenyl)phosphinomethyl-4-tosyloxypyrrolidine (VIIB) was obtained as an amorphous solid. $[\alpha]_D^{23} = -85.0°$ (c=0.7, benzene).

In a separate reaction vessel and under argon atmosphere, diphenylphosphine (1.25 g) was dissolved in THF (20 ml) and the solution was cooled to −30° C. 1.6M-n-butyllithium-hexane solution (4.6 ml) was added thereto and the mixture was stirred for 15 minutes. To the mixture was added dropwise at −30° C. compound (VIIB) (3.5 g) dissolved in THF (40 ml). The mixture was stirred overnight and subjected to filtration after celite (filter aid) was added thereto. The filtrate was concentrated and, after addition of a cold saturated aqueous solution of sodium bicarbonate, extracted with benzene. The benzene layer was dried over anhydrous magnesium sulfate and concentrated. The residue was purified by column chromatography on alumina (toluene-toluene/ethyl acetate) whereby 2.93 g of (2S,4S)-N-tert.-butoxycarbonyl-2-bis(4-dimethylaminophenyl)phosphinomethyl-4-diphenylphosphinopyrrolidine (Ic) was obtained as an amorphous solid. $[\alpha]_D^{23} = -40.66°$ (c=0.7, benzene)

EXAMPLE 3

Under argon atmosphere, bis(2-methoxyphenyl)phosphine (2.38 g) was dissolved in THF (30 ml) and the solution was cooled to −30° C. 1.6M-n-butyllithium-hexane solution (6.6 ml) was added thereto and the mixture was stirred for 30 minutes. (2S,4R)-N-tert.-butoxycarbonyl-4-tosyloxy-2-tosyloxymethylpyrrolidine (VI) (1.27 g) dissolved in THF (30 ml) was added dropwise and the mixture was stirred overnight at −30° C. The mixture was then subjected to filtration after celite (filter aid) was added thereto. The filtrate was concentrated and, after addition of cold saturated aqueous solution of sodium bicarbonate, extracted with benzene. The benzene layer was dried over anhydrous magnesium sulfate and then concentrated. The residue was purified by column chromatography on silica gel (toluene-toluene/ethyl acetate) whereby 1.11 g of (2S,4S)-N-tert.-butoxycarbonyl-4-bis(2-methoxyphenyl)phosphino-2-bis(2-methoxyphenyl)phosphinomethylpyrrolidine (see formula Id) was obtained as an amorphous solid. $[\alpha]_D^{23} = -85.5°$ (c=1.02, benzene)

EXAMPLE 4

In the same manner as described in Example 3 but using bis(3-methoxyphenyl)phosphine (392 mg) instead of the bis(2-methoxyphenyl)phosphine used therein, the reaction, after-treatment and purification were carried out whereby 137 mg of (2S,4S)-N-tert.-butoxycarbonyl- 4-bis(3-methoxyphenyl)phosphino-2-bis(3-methoxyphenyl)phosphinomethylpyrrolidine (Ie) was obtained as an amorphous solid. $[\alpha]_D^{23} = -40.6°$ (c=1.02, benzene)

EXAMPLE 5

In the same manner as described in Example 3 but using bis(2,4-dimethoxyphenyl)phosphine (612 mg) instead of the bis(2-methoxyphenyl)phosphine used therein, the reaction, after-treatment and purification were carried out whereby 206 mg of (2S,4S)-N-tert.-butoxycarbonyl-4-bis(2,4-dimethoxyphenyl)phosphino-2-bis(2,4-dimethoxyphenyl)phosphinomethylpyrrolidine (see formula If) was obtained as an amorphous solid. $[\alpha]_D^{20} = -90.5°$ (c=0.76, benzene)

Elementary Analysis Found: C=63.55, H=6.73, N=1.75%; Calcd: C=63.82, H=6.68, N=1.61%.

EXAMPLE 6

(2S,4R)-N-tert.-butoxycarbonyl-4-hydroxy-2-hydroxymethylpyrrolidine (VIII) (21.7 g) was dissolved in THF (400 ml). To the solution were added triethylamine (16.8 ml), tert.-butyldimethylchlorosilane (16.6 g) and 4-dimethylaminopyridine (0.5 g), and the mixture was stirred overnight at room temperature. The mixture was concentrated under reduced pressure and water (100 ml) was added to the residue. The mixture was extracted with ethyl acetate. The ethyl acetate layer was washed with a saturated aqueous solution of sodium chloride, dried over anhydrous magnesium sulfate and concentrated under reduced pressure until dryness. The residue was dissolved in pyridine (250 ml) and the solution was cooled to $-20°$ C. p-Toluenesulfonyl chloride (22.9 g) was added thereto and the mixture was stirred overnight. After addition of 10% hydrochloric acid (1,000 ml), the mixture was extracted with ethyl acetate. The ethyl acetate layer was washed successively with water, a saturated aqueous solution of sodium bicarbonate and a saturated aqueous solution of sodium chloride, dried over anhydrous magnesium sulfate, and concentrated under reduced pressure. The residue was purified by column chromatography on silica gel whereby 36.9 g of (2S,4R)-N-tert.-butoxycarbonyl-2-tert.-butyldimethylsilyloxymethyl-4-tosyloxypyrrolidine (X) was obtained.

In a separate reaction vessel and under argon atmosphere, bis(4-methoxyphenyl)phosphine (4.30 g) was dissolved in THF (80 ml) and the solution was cooled to $-40°$ C. 1.6M-n-butyllithium-hexane solution (15 ml) was added thereto and the mixture was stirred for 15 minutes to give a phosphine anion solution.

In another separate reaction vessel, (2S,4R)-N-tert.-butoxycarbonyl-2-tert.-butyldimethylsilyloxymethyl-4-tosyloxypyrrolidine (X) (8.7 g) was dissolved in THF (200 ml) and the solution was cooled to $-20°$ C. To this cooled solution was added dropwise the phosphine anion solution prepared above. The mixture was stirred at $-20°$ C. for 2 hours and, after addition of celite (filter aid), subjected to filtration. The filtrate was concentrated and, after addition of a cold saturated aqueous solution of sodium bicarbonate, extracted with benzene. The benzene layer was dried over anhydrous magnesium sulfate and concentrated. The residue was dissolved in methanol (200 ml) and 10% aqueous hydrogen peroxide (12 g) was added dropwise to the solution. The mixture was stirred at 0° C. for 1 hour and then at room temperature for 1 hour. The solvent was evaporated off and water was added thereto. The mixture was extracted with methylene chloride and the methylene chloride layer was washed successively with water, a saturated aqueous solution of sodium bicarbonate and a saturated aqueous solution of sodium chloride, dried over anhydrous magnesium sulfate and concentrated under reduced pressure. The residue was purified by column chromatography on silica gel whereby 10.44 g of (2S,4S)-N-tert.-butoxycarbonyl-2-tert.-butyldimethylsilyloxymethyl-4-bis(4-methoxyphenyl)phosphinylpyrrolidine (XI) was obtained as an amorphous solid. $[\alpha]_D^{20} = -58.6°$ (c=0.74, ethanol)

In a separate reaction vessel, compound (XI) (9.69 g) was dissolved in THF (300 ml) and tetrabutylammonium fluoride (15 g) was added thereto. The mixture was stirred at room temperature for 3 hours. The solvent was evaporated off and water was added thereto. The mixture was extracted with methylene chloride and the methylene chloride layer was washed successively with water, a saturated aqueous solution of sodium bicarbonate and a saturated aqueous solution of sodium chloride, dried over anhydrous magnesium sulfate and concentrated under reduced pressure whereby 6.77 g of (2S,4S)-N-tert.-butoxycarbonyl-2-hydroxymethyl-4-bis(4-methoxyphenyl)phosphinylpyrrolidine (XII) was obtained as an oil.

$[\alpha]_D^{20} = -19.4°$ (c=0.64, ethanol) IR: 1680 (CO), 3340 cm$^{-1}$ (OH)

Compound (XII) (5.55 g) was dissolved in pyridine (120 ml) and the solution was cooled to $-20°$ C. p-Toluenesulfonyl chloride (2.85 g) was added and the mixture was stirred overnight. 10% hydrochloric acid (500 ml) was added and the mixture was extracted with ethyl acetate. The ethyl acetate layer was washed successively with water, a saturated aqueous solution of sodium bicarbonate and a saturated aqueous solution of sodium chloride, dried over anhydrous magnesium sulfate and concentrated under reduced pressure. The residue was purified by column chromatography on silica gel whereby 5.02 g of (2S,4S)-N-tert.-butoxycarbonyl-4-bis(4-methoxyphenyl)phosphinyl-2-tosyloxymethylpyrrolidine (XIII) was obtained as an amorphous solid.

NMR δ(CDCl$_3$): 1.35 (9H,s), 2.4 (3H,s), 3.75 (6H,s)

In a separate reaction vessel and under argon atmosphere, bis(2-methoxyphenyl)phosphine (2.46 g) was dissolved in THF (50 ml) and the solution was cooled to $-40°$ C. 1.6M-n-butyllithium-hexane solution (7.5 ml) was added thereto and the mixture was stirred for 15 minutes to give a phosphine anion solution.

In another separate reaction vessel, compound (XIII) (1.54 g) was dissolved in THF (100 ml) and DMF (40 ml), and the solution was cooled to $-20°$ C. To this cooled solution was added dropwise the phosphine anion solution prepared above. The mixture was stirred at $-20°$ C. for 4 hours and subjected to filtration after celite (filter aid) was added thereto. The filtrate was concentrated and, after addition of a cold saturated aqueous solution of sodium bicarbonate, extracted with ethyl acetate. The ethyl acetate layer was dried over anhydrous magnesium sulfate and then concentrated. The residue was dissolved in methanol (100 ml), and 10% aqueous hydrogen peroxide (5.0 g) was added dropwise to the solution under ice-cooling. The mixture was stirred at 0° C. for 1 hour and then at room temperature for 1 hour. The solvent was evaporated off and water is added. The mixture was extracted with methylene chloride and the methylene chloride layer was washed successively with water, a saturated aqueous solution of sodium bicarbonate and a saturated aqueous solution of sodium chloride, dried over anhydrous magnesium sulfate and concentrated under reduced pressure. The residue was purified by column chromatography on silica gel whereby 1.49 g of (2S,4S)-N-tert.-butoxycarbonyl-2-bis(2-methoxyphenyl)phosphinylmethyl-4-bis(4-methoxyphenyl)phosphinylpyrrolidine (XIV) was obtained as an amorphous solid.

In another separate reaction vessel, trifluoroacetic acid (20 ml) was ice-cooled and compound (XIV) (1.41 g) was added thereto. The mixture was stirred at 0° C. for 2 hours. After addition of water, the mixture was extracted with methylene chloride and the methylene chloride layer was washed successively with water, a saturated aqueous solution of sodium bicarbonate and a saturated aqueous solution of sodium chloride, dried over anhydrous magnesium sulfate and concentrated under reduced pressure whereby 1.22 g of (2S,4S)-2-bis(2-methoxyphenyl)phosphinylmethyl-4-bis(4-methoxyphenyl)phosphinylpyrrolidine (XV) was obtained as an oil.

IR: 3250 cm$^{-1}$ (NH).

Compound (XV) (242 mg) and triethylamine (170 mg) were dissolved in acetonitrile (16 ml) and the air in the reaction vessel was thoroughly replaced by nitrogen. Under ice-cooling, trichlorosilane (216 mg) dissolved in acetonitrile (4 ml) was added dropwise. The mixture was refluxed for 3 hours and the reaction mixture was cooled down to room temperature and concentrated under reduced pressure. The residue was dissolved in benzene (30 ml) and a 30% aqueous solution of caustic soda (20 ml) was added under ice-cooling. The mixture was stirred at 50°-60° C. for 30 minutes under nitrogen atmosphere. The benzene layer was separated and the aqueous layer was extracted with benzene. The benzene layers were combined, washed with water, dried over anhydrous magnesium sulfate and concentrated under reduced pressure whereby 163 mg of (2S,4S)-2-bis(2-methoxyphenyl)phosphinomethyl-4-bis(4-methoxyphenyl)phosphinopyrrolidine (Ib) was obtained. This product was dissolved in methylene chloride (2.8 ml) and triethylamine (31 mg) was added thereto. Under nitrogen atmosphere, di-tert.-butyl dicarbonate (68 mg) dissolved in methylene chloride (5 ml) was added dropwise and the mixture was stirred at room temperature for 3 hours. The reaction mixture was concentrated and purified by column chromatography on silica gel whereby 143 mg of (2S,4S)-N-tert.-butoxycarbonyl-2-bis(2-methoxyphenyl)phosphinomethyl-4-bis(4-methoxyphenyl)phosphinopyrrolidine (Ig) was obtained as an amorphous solid.

$[\alpha]_D^{20} = -49.8°$ (c=0.74, benzene) IR: 1700 cm$^{-1}$ (CO)

Elementary analysis Found: C=67.75, H=6.73, N=2.08%; Calcd.: C=67.98, H=6.75, N=1.90%.

EXAMPLE 7

Under argon atmosphere, diphenylphosphine (0.64 g) was dissolved in THF (40 ml) and the solution was cooled to −40° C. 1.6M-n-butyllithium-hexane solution (2.6 ml) was added and the mixture was stirred for 15 minutes to give a phosphine anion solution.

In a separate reaction vessel, (2S,4R)-N-tert.-butoxycarbonyl-4-tosyloxy-2-tosyloxymethylpyrrolidine (1.50 g) was dissolved in THF (10 ml) and the solution was cooled to −50° C. To this cooled solution was added dropwise the phosphine anion solution for 5 hours, during which the temperature rose from −50° C. to −20° C. The reaction mixture thus obtained will hereinafter referred to as "reaction mixture (A)".

In a separate reaction vessel and under argon atmosphere, bis(3,5-dimethyl-4-methoxyphenyl)phosphine (1.7 g) was dissolved in THF (30 ml) and the solution was cooled to −35° C. 1.6M-n-butyllithium-hexane solution (4.2 ml) was added thereto and the mixture was stirred for 30 minutes. The resulting solution of bis(3,5-dimethyl-4-methoxyphenyl)phosphinolithium in THF was added dropwise at −35° C. to the reaction mixture (A) mentioned above. The mixture was stirred for 5 hours, during which the temperature rose to −10° C. The mixture was subjected to filtration after celite (filter aid) was added thereto. The filtrate was concentrated and, after addition of a cold saturated aqueous solution of sodium bicarbonate, extracted with ethyl acetate. The organic layer was dried over anhydrous magnesium sulfate and concentrated. The residue was purified by column chromatography on silica gel (benzene-benzene/ethyl acetate) whereby 1.00 g of (2S,4S)-N-tert.-butoxycarbonyl-4-bis(3,5-dimethyl-4-methoxyphenyl)phosphino-2-diphenylphosphinomethylpyrrolidine (Ia) was obtained as an amorphous solid.

$[\alpha]_D^{23} = -25.9°$ (c=0.5, benzene)

EXAMPLE 8

Under argon atmosphere, bis(3,5-dimethyl-4-methoxyphenyl)phosphine (1.58 g) was dissolved in THF (30 ml) and the solution was cooled to −40° C. 1.6M-n-butyllithium-hexane solution (3.9 ml) was added thereto and the mixture was stirred for 15 minutes to give a phosphine anion solution.

In a separate reaction vessel, (2S,4R)-N-tert.-butoxycarbonyl-4-tosyloxy-2-toxyloxymethylpyrrolidine. (0.69 g) was dissolved in THF (10 ml) and the solution was cooled to −40° C. To this cooled solution was added dropwise the phosphine anion solution prepared above. The mixture was stirred overnight at −40° C. and, after addition of celite (filter aid), subjected to filtration. The filtrate was concentrated and, after addition of a cold saturated aqueous solution of sodium bicarbonate, extracted with ethyl acetate. The organic layer was dried over anhydrous magnesium sulfate and then concentrated. The residue was purified by column chromatography on silica gel (benzene-benzene/ethyl acetate) whereby 727 mg of (2S,4S)-N-tert.-butoxycarbonyl-2-bis(3,5-dimethyl-4-methoxyphenyl)phosphinomethyl-4-bis(3,5-dimethyl-4-methoxyphenyl)-phosphinopyrrolidine (Ii) was obtained as an amorphous solid.

$[\alpha]_D^{21} = -28.2°$ (c=1.0, benzene)

In the following are exemplified the asymmetric synthesis according to the invention.

Synthesis: Nos. 1–5

0.0025 m-mol of rhodium-1,5-cyclooctadienechloride complex, 0.0065 m-mol of one of the asymmetric ligand compounds indicated in Table 1 and 0.25 m-mol of triethylamine were dissolved in 20 ml of ethanol, and 5 m-mol of α-acetamidocinnamic acid was added to the solution. The mixture was stirred for 20 hours at 50° C. and under a hydrogen atmosphere of 20 atm. The reaction mixture was concentrated under reduced pressure and then dissolved in 0.5N aqueous solution of caustic soda. Insolubles were filtered off and the filtrate was made acid with diluted hydrochloric acid and extracted with ether. The organic layer was washed with water and dried. The solvent was distilled off to obtain optically active (R)-N-acetylphenylalanine. The results of Synthesis Nos. 1–5 are shown in Table 1.

TABLE 1

| No. | Asymmetric Ligand | Starting Material/Rh | Conversion | Optical Yield |
|---|---|---|---|---|
| 1 | BPPM | 1,000 | 100% | 78% ee |
| 2 | Id | 1,000 | 100 | 98 |
| 3 | Ie | 1,000 | 100 | 85 |
| 4 | If | 1,000 | 100 | 90 |
| 5 | Ig | 1,000 | 100 | 98 |

Synthesis Nos. 6–8

0.0025 m-mole of rhodium-1,5-cyclooctadienechloride complex and 0.0065 m-mole of one of the asymmetric ligand compounds indicated in Table 2 were dissolved in 10 ml of THF, and 5 m-mole of ketopantolactone was added thereto. Reduction was carried out at a hydrogen atmosphere of 50 atm. The mixture was stirred at 50° C. for 45 hours. The reaction mixture was concentrated under reduced pressure and distilled under reduced pressure to obtain optically active (R)-(−)-pantolactone. The results are shown in Table 2.

TABLE 2

| No. | Asymmetric Ligand | Starting Material/Rh | Conversion | Optical Yield |
|---|---|---|---|---|
| 6 | BPPM | 1,000 | 44% | 72% ee |
| 7 | Ia | 1,000 | 100 | 89 |
| 8 | Ic | 1,000 | 78 | 69 |

Synthesis No. 9

0.005 m-mole of rhodium-dinorbornadieneperchlorate, 0.0065 m-mole of (2S,4S)-N-tert.-butoxycarbonyl-2-bis(3,5-dimethyl-4-methoxyphenyl)phosphinomethyl-4-bis(3,5-dimethyl-4-methoxyphenyl)phosphinopyrrolidine (Ii) and 0.25 m-mole of triethylamine were dissolved in 20 ml of ethanol and 5 m-mol of α-acetamidocinnamic acid was added to the solution. The mixture was stirred for 20 hours at 50° C. and under a hydrogen pressure of 20 atm. The reaction mixture was concentrated under reduced pressure and then dissolved in 0.5N aqueous solution of caustic soda. Insolubles were filtered off and the filtrate was made acid with diluted hydrochloric acid and extracted with ether. The organic layer was washed with water and dried. The solvent was distilled off to obtain optically active (R)-N-acetylphenylalanine. Conversion 100%; optical yield 98%.

Synthesis No. 10.

In the same manner as described in Synthesis No. 9 but using α-acetamido-β-(3,4-methylenedioxyphenyl)acrylic acid instead of the α-acetamidocinnamic acid used therein, (R)-N-acetyl-β-(3,4-methylenedioxyphenyl)alanine was obtained. Conversion 100%; optical yield 92%.

Synthesis No. 11

In the same manner as described in Synthesis No. 9 but using α-acetamidocinnamic acid instead of the α-acetamidocinnamic acid, (R)-N-acetylalanine was obtained. Conversion 100%; asymmetric yield 95%.

Synthesis No. 12

In the same manner as described in Synthesis No. 9 but using α-acetamido-β,β-dimethylacrylic acid instead of α-acetamidocinnamic acid used therein, (R)-N-acetylleucine was obtained. Conversion 100%; optical yield 95%.

What is claimed is:

1. Phosphinopyrrolidine compounds of the formula:

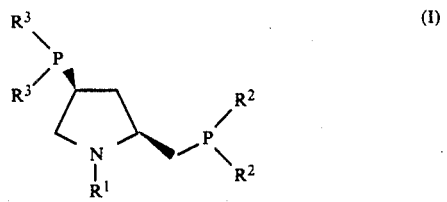

(I)

or

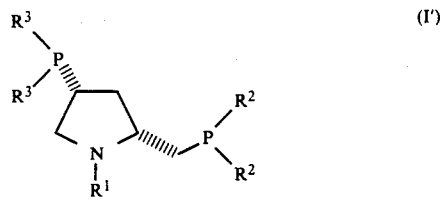

(I')

wherein $R^1$ is hydrogen, $-COA^1$, $-COOA^2$, $-CONHA^3$, $-SO_2A^4$ or $-PO(A^5)_2$, $A^1$, $A^2$, $A^3$, $A^4$ and $A^5$ each represents independently alkyl or aryl, $R^2$ is phenyl, di(lower-alkyl)aminophenyl, lower-alkoxyphenyl or 3,5-dimethyl-4-methoxyphenyl, and $R^3$ is phenyl, di(lower-alkyl)aminophenyl, lower-alkoxyphenyl or 3,5-dimethyl-4-methoxyphenyl, with the proviso that $R^2$ and $R^3$ may not simultaneously be phenyl, p-di(lower-alkyl)aminophenyl or p-lower-alkoxyphenyl.

2. Phosphinopyrrolidine compounds of the formula (I) or (I') as claimed in claim 1, wherein $R^2$ is phenyl and $R^3$ is di(lower-alkyl)aminophenyl or lower-alkoxyphenyl.

3. Phosphinopyrrolidine compounds of the formula (I) or (I') as claimed in claim 1, wherein $R^2$ and $R^3$ are different from each other and each represents di(lower-alkyl)aminophenyl and/or lower-alkoxyphenyl.

4. Phosphinopyrrolidine compounds of the formula (I) or (I') as claimed in claim 1, wherein $R^2$ and $R^3$ are the same and represent di(lower-alkyl)aminophenyl or lower-alkoxyphenyl, with the proviso that $R^2$ and $R^3$ may not simultaneously be p-di(lower-alkyl)aminophenyl or p-lower-alkoxyphenyl.

* * * * *